US006784336B2

(12) United States Patent
Eggan et al.

(10) Patent No.: US 6,784,336 B2
(45) Date of Patent: Aug. 31, 2004

(54) METHOD OF PRODUCING MUTANT MICE

(75) Inventors: Kevin C. Eggan, Cambridge, MA (US); Rudolf Jaenisch, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/755,003

(22) Filed: Jan. 5, 2001

(65) Prior Publication Data

US 2002/0062493 A1 May 23, 2002

Related U.S. Application Data

(60) Provisional application No. 60/255,970, filed on Dec. 15, 2000, and provisional application No. 60/234,378, filed on Sep. 20, 2000.

(51) Int. Cl.⁷ .................... C12N 15/06; A01K 67/00

(52) U.S. Cl. .......................... 800/21; 800/18

(58) Field of Search .................... 800/21, 18

(56) References Cited

U.S. PATENT DOCUMENTS

| | | | |
|---|---|---|---|
| 5,942,435 A | 8/1999 | Wheeler | |
| 6,492,575 B1 | 12/2002 | Wagner et al. | |
| 2002/0078470 A1 | 6/2002 | Eggan et al. | .............. 800/18 |

FOREIGN PATENT DOCUMENTS

WO     WO 98/06834     2/1998

OTHER PUBLICATIONS

Ueda et al. Production of mice entirely derived from embryonic stem (ES) cell with many passages by coculture of ES cells with cytochalasin B induced tetraploid embryos. Exp Anim. Jul. 1995;44(3):205–10.*
Doetschman et al. Interpretation of phenotype in genetically engineered mice. Lab Anim Sci. Apr. 1999;49(2):137–43.*
Wall, Transgenic livestock: progress and prospects for the future. Theriogenology 1996 45:57–68.*
Yagi et al. A novel ES cell line, TT2, with high germline–differentiating potency. Anal Biochem. Oct. 1993 ;214(1):70–6.*
Sigmund, Viewpoint: are studies in genetically altered mice out of control? Arterioscler Thromb Vasc Biol. 2000 Jun.;20(6):1425–9.*
English translation of Uchida, M., et al.,*Animal Science and Technology, 66*(4):361–367 (1995); cited as reference W on PTO–892 attached to Paper No. 8.
Nagy, Andráet al., "Embryonic Stem Cells Alone are able to Support Fetal Development in the Mouse," *Development*, 110:815–821 (1990).
Wang, Zhao–Qi et al., "Generation of Completely Embryonic Stem Cell–Derived Mutant Mice Using Tetraploid Blastocyst Injection," *Mechanisms of Development*, 62:137–145 (1997).

Nagy, András et al., "Derivation of Completely Cell Culture–Derived Mice from Early–Passage Embryonic Stem Cells," *Proc. Natl. Acad. Sci. USA*, 90:8424–8428 (Sep. 1993).
You, Yun et al., "Utility of C57BL/6J x 129/Sv$^{Jae}$ Embryonic Stem Cells for Generating Chromosomal Deletions: Tolerance to Γ Radiation and Microsatellite Polymorphism," *Mammalian Genome*, 9:232–234 (1998).
James, R.M. et al., "Electrofusion of Mouse Embryos Results in Uniform Tetrploidy and not Tetraploid/Diploid Mosaicism," *Genet. Res.*, 60(3) :185–194 (Dec. 1992).
Rideout, W.M. et al., Generation of Mice from Wild–Type and Targeted ES Cells by Nuclear Cloning, *Nat. Genet.*, 24(2) :109–110 (Feb. 2000).
Ueda, O. et al., "Production of Mice Entirely Derived from Embryonic Stem (ES) Cell with Many Passages by Coculture of ES Cells with Cytochalasin B Induced Tetraploid Embryos," *Exp. Anim.*, 44(3) :205–210 (Jul. 1995).
James, R.M. et al., "Restricted Distribution of Tetraploid Cells in Mouse Tetraploid ⇆ Diploid Chimaeras," *Developmental Biology*, 167:213–226 (1995).
You, Yun et al., "Chromosomal Deletion Complexes in Mice by Radiation of Embryonic Stem Cells," *Nature Genetics*, 15:285–288 (Mar. 1997).
Everett, C.A. et al., "The Influence of Ploidy on the Distribution of Cells in Chimaeric Mouse Blastocysts," *Zygote*, 4(1) :59–66 (1996).
Prather, R.S. et al., "Characterization of DNA Synthesis During the 2–Cell Stage and the Production of Tetraploid Chimeric Pig Embryos," *Molecular Reproduction and Development*, 45:38–42 (1996).
Nagy, A., and Rossant, J., "Production of Completely ES Cell–Derived Fetuses," In *Gene Targeting*, A.L. Joyner, ed. (NY: Oxford University Press, Inc.), pp. 147–179 (1993).
Eggan, K. et al. (May 1, 2001), "Hybrid Vigor, Fetal Overgrowth, and Viability of Mice Derived by Nuclear Cloning and Tetraploid Embryo Complementation," *Proc. Natl. Acad. Sci. USA*, 10.1073/pnas.101118898.
Eggan, K. et al., "X–Chromosome Inactivation in Cloned Mouse Embryos," *Science*, 290(5496) :1578–1581 (2000).
Soriano, P., "Generalized lacZ Expression with the ROSA26 Cre Reporter Strain," *Nature Genetics*, 21:70–71 (1999).
Lamar, E.E et al., "Y Encoded Species Specific DNA in Mice Evidence that the Y Chromosome Exists in 2 Polymorphic Forms in Inbred Strains," *Cell*, 37(1) :171–177 (1984).

(List continued on next page.)

Primary Examiner—Anne-Marie Falk
Assistant Examiner—Daniel M. Sullivan
(74) *Attorney, Agent, or Firm*—Hamilton, Brook, Smith & Reynolds, P.C.

(57) ABSTRACT

A method of producing mutant/targeted non-human mammals, such as mutant mice that does not require production of chimera and permits the introduction of multiple mutations in embryos and, thus, avoids the necessity of breeding to combine all of the desired mutations in a single animal. The method is efficient in producing ES mice.

17 Claims, No Drawings

OTHER PUBLICATIONS

Farley, F.W. et al., "Widespread Recombinase Expression Using FLPeR (flipper) Mice," *Genesis The Journal of Genetics and Development*, 28(3–4):106–110 (2000).

Rideout, W.M. et al., "Nuclear Cloning and Epigenetic Reprogramming of the Genome," *Science*, 293(5532):1093–1098 (2001).

Eggan, K. et al., "Male and Female Mice Derived from the Same Embryonic Stem Cell Clone by Tetraploid Embryo Complementation," *Nature Biotechnology*, 20(5):455–459 (2002).

* cited by examiner

METHOD OF PRODUCING MUTANT MICE

RELATED APPLICATION(S)

This application claims the benefit of the filing date of U.S. provisional application 60/234,378, entitled "Method of Producing Non-Human Mammals", by Kevin C. Eggan and Rudolf Jaenisch, filed Sep. 20, 2000 and the filing date of U.S. provisional application 60/255,970, entitled "Method of Producing Non-Human Mammals", by Kevin C. Eggan and Rudolf Jaenisch, filed Dec. 15, 2000. The entire teachings of the referenced applications are incorporated herein by reference.

GOVERNMENT SUPPORT

Work described herein was supported, in whole or in part, by National Institutes of Health Grants No. 5-R35-CA44339 and RO1-CA84198. The United States government has certain rights in the invention.

BACKGROUND OF THE INVENTION

In the past two decades, considerable effort has been invested in producing non-human mammals, such as mutant or transgenic mammals, such as mice, and during that time, a variety of methods have been developed. In order to produce a desired mutant animal, such as a mouse, using any of the presently available methods, one must first produce chimeras and breed the chimeras to produce homozygous offspring; production of offspring which are not chimeric requires two breeding cycles for each gene. This is the case for each mutation to be introduced and, if offspring exhibiting more than one mutation are desired, additional breeding cycles are required. For example, if mutant mice bearing six different alterations (e.g., six different genes) are to be produced, approximate breeding time will be two years. Producing desired genetically manipulated mammals, even those for which the breeding cycle is relatively brief, requires considerable time, as well as resources, using current methods. It would be very valuable if a more efficient method of producing mutant mammals, such as mice, were available.

SUMMARY OF THE INVENTION

The present invention relates to methods of producing non-human mammals, which can be mutant non-human mammals or non-mutant non-human mammals, such as mice, that do not require production of chimera or chimeric offspring (offspring that consist of cells that are derived from more than one zygote). The invention is a method of producing non-human mammals, such as mutant or non-mutant mice, by tetraploid blastocyst complementation using non-inbred pluripotent cells, such as non-inbred ES cells.

The present method makes it possible to include multiple mutations or alterations in the same pluripotent cells (e.g., embryonic stem (ES) cells) before producing an animal from the ES cells. The present invention relates to methods of producing non-human mammals that, thus, avoid the time-consuming step of breeding chimera to produce the desired offspring. As is evident from the work described herein, mutant or targeted offspring, particularly mice, that are entirely derived from ES cells and survive postnatally have been produced without the need to produce chimeric intermediates. Mutations introduced into the non-inbred pluripotent cells can be non-random or targeted alterations or can be random or non-targeted alterations. The products of either approach are referred to herein as mutant. In those embodiments in which mutations are non-random or targeted, the resulting products can also be referred to as targeted (e.g., targeted ES cells, targeted non-human mutant mammals, such as targeted mutant mice). Alterations can be of a variety of types, including deletion, addition, substitution, or modification of all or a portion of DNA (e.g., a gene, regulatory element) in the ES cells. These alterations include addition of a gene or gene portion not normally present in the ES cells. Non-mutant mice that are derived entirely from ES cells and survive postnatally can also be produced using the method described. The present methods of producing mice, particularly mutant mice, make it possible to produce offspring, particularly mutant offspring, very efficiently, particularly in comparison with other methods.

The present invention also relates to a method for deriving fertile XO female mice from non-inbred (F1) mouse male ES cells and a method of deriving males and females carrying all genetic alterations introduced into a single non-inbred ES clone, such as a targeted non-inbred mouse ES cell clone. Breeding of the mutant males and females allows the production of a mutant mouse strain derived from a single non-inbred ES cell clone, such as a targeted (e.g., multiply targeted ES cell clone), without outcrossing the mutant animal with a wildtype partner, as is required in presently available methods.

The present invention also relates to non-human mammals, particularly mutant non-human mammals, such as mutant mice, produced by the methods; cells obtained from the mutant or non-mutant non-human mammals and cell lines produced from these cells. A particular embodiment is cells obtained from mutant or non-mutant mice produced by a method of the present invention; cells obtained from the mice and cell lines produced from such cells. The invention further relates to a method of producing blastocysts useful in the method of producing mutant or non-mutant mammals, such as mouse blastocysts (non-mutant or mutant) useful for producing non-mutant or mutant mice by the method described herein and blastocysts produced by the method.

In particular embodiments, mutant non-human mammals (e.g., mutant mice) are produced to mimic or serve as a model for a condition (e.g., a neurological, muscular or respiratory condition, cancer, viral infection, arthritis,) that occurs in another species, such as in humans. They are used to identify new drugs that have a therapeutic or preventive effect on the condition or assess the ability of known drugs to act as therapeutics or preventatives. Thus, the present invention encompasses methods in which the mutant non-human mammals (particularly mutant mice) are used, such as in a method of screening to identify a new drug that inhibits the occurrence of (prevents the onset, reduces the extent or severity of) or reverses a condition caused by or associated with the genetic alteration(s) and a method of screening known drugs for those that inhibit onset of or reverse such conditions. Drugs identified by methods in which the mutant mammals of the present invention are used are also the subject of this invention. These include drugs that inhibit onset of a condition (prevent the onset or reduce the extent to which the condition is established or severity of the condition), referred to as preventatives or prophylactic drugs and drugs that reverse (partially or completely) or reduce the extent or duration of the condition once it has occurred.

DETAILED DESCRIPTION OF THE INVENTION

As described herein, Applicants have demonstrated that genetic background is a crucial parameter controlling postnatal survival of offspring that are entirely derived from ES cells. That is, heterozygosity of the genome of the pluripotent donor cell (e.g., heterozygosity of the donor ES cell genome) is critical for postnatal survival of offspring whose development is achieved without the contribution of normal cells derived from the host embryo. Further, Applicants have demonstrated that non-human mammals, particularly mice, can be generated without the need to first create a chimeric intermediate. The ability to derive offspring (e.g., mice) directly from ES cells without the need to produce chimeric intermediates is a distinct advantage, not only because it avoids the time consuming and expensive step of producing chimera, but also because it facilitates the generation of offspring with multiple genetic alterations. The generation of F1 ES cell-tetraploid mice provides a simple procedure for directly deriving animals with complex genetic alterations without the need to create a chimeric intermediate. The tetraploid technology in combination with the use of F1 cells allows assembly or production of multiple genetic alterations in the same ES cell clone by consecutive gene targeting cycles in vitro. The resulting multiply targeted F1 ES cell clone is introduced into tetraploid blastocysts to produce an embryo that is then transferred to an appropriate foster mother and permitted to develop to term. Thus, a transgenic animal with one or multiple desired or selected genetic alterations can be generated without the need for production of chimeric founders and outbreeding with wild type mice.

Also described herein is a strategy for deriving fertile XO females from F1 male ES cells and a method of breeding a mutant mouse strain derived from a given multiply targeted ES cell clone without outcrossing the mutant animal with a wild type partner. This avoids time consuming and costly outcrossing, which would otherwise be necessary. Because each F1 ES cell line is of a given sex—usually male—it would not be possible to breed a mutant mouse strain derived from a given multiply targeted ES cell clone without outcrossing, using presently available methods. As described herein, however, outcrossing is no longer required, in view of the fact that it is possible to generate mutant males and females from a single targeted male ES cell clone by selection for loss of one Y chromosome, resulting in generation of XO ES cells. In one embodiment, a negative selection marker (e.g., a negative selection gene, such as a Herpes Tk gene) is introduced into the Y chromosome of F1 male ES cells, as described further below, and the resulting cells are subject to selection with an agent (e.g., gancyclovir) which kills all cells carrying the Y chromosome. Cells that are not killed have lost the Y chromosome and, thus, are XO. This enables subsequent generation of males and females carrying identical genetic alterations, as described further below.

The invention described herein relates to a method of producing non-human mammals, which can be mutant or non-mutant animals, such as mutant or non-mutant mice. As described herein, it has now been shown that mutant non-human mammals can be produced without the intermediate step of producing chimeric animals which, in presently available methods, must be bred to produce the desired mutants. In particular, targeted or mutant mice have been produced and the present invention is described in detail by describing their production. However, the present invention is useful to produce mutants or non-mutants of any non-human mammal for which embryonic stem (ES) cells can be obtained.

The invention is, in one embodiment, a method of producing a non-human mammal. The method comprises introducing non-inbred pluripotent cells, such as non-inbred ES cells, into tetraploid blastocysts of the same mammalian species, under conditions that result in production of an embryo (at least one/one or more embryo) and transferring the resulting embryo(s) into an appropriate foster mother, such as a pseudopregnant female of the same mammalian species. The resulting female is maintained under conditions that result in development of live offspring, thereby producing a mutant non-human mammal. The resulting non-human mammal is derived from a single zygote (that which originally gave rise to the ES cells). Such mammals are referred to herein as ES non-human mammals.

In another embodiment, the invention is a method of producing a mutant non-human mammal. The method comprises introducing non-inbred pluripotent cells, such as non-inbred ES cells, comprising at least one mutation or alteration into tetraploid blastocysts of the same mammalian species, under conditions that result in production of an embryo (at least one/one or more embryo) and transferring the resulting embryo(s) into an appropriate foster mother, such as a pseudopregnant female of the same mammalian species. The resulting female is maintained under conditions that result in development of live offspring, thereby producing a mutant non-human mammal. The resulting mutant non-human mammal is derived from a single zygote (that which originally gave rise to the ES cells). Such mammals are referred to herein as mutant ES non-human mammals. The mutations or alterations can be non-random or targeted or, alternatively, can be introduced randomly or in a non-targeted manner.

A specific embodiment of the present invention is a method of producing a targeted or mutant mouse, comprising: (a) introducing mouse non-inbred pluripotent cells comprising at least one alteration in genomic DNA into mouse blastocysts, preferably tetraploid blastocysts, thereby producing mouse blastocysts containing mouse non-inbred pluripotent cells; (b) maintaining the product of (a) under conditions that result in production of embryos; (c) introducing an embryo or embryos (at least one/one or more embryos) into a foster mother, such as a pseudopregnant female mouse; and (d) maintaining the female into which the embryo(s) were introduced under conditions that result in development of live offspring, thereby producing a mutant mouse. The mutant mouse is also referred to herein as a mutant ES mouse. In one embodiment, the non-inbred mouse pluripotent cells are non-inbred mouse ES cells, such as F1 cells derived from two different strains of mice or F2, F3 F4, etc. cells that can be derived from parents after consecutive brother—sister matings. Alternatively, such cells can be derived from parents after backcrossing an F1 strain to one of the parent strain to obtain the first backcross generation (N1) and by further backcrossing to obtain N2, N3, N4, etc. backcross generations. As used herein, the term non-inbred ES cells encompasses all of the hereinabove described ES cells. Derivation of non-inbred ES cells, with specific reference to production of mouse ES cells, is described in detail in the Exemplification.

In a further embodiment, the invention is a method of producing a non-mutant mouse, referred to as a non-mutant ES mouse. The method is carried out as described above for the production of mutant ES mice, except that DNA in the non-inbred pluripotent cells, such as non-inbred ES cells (e.g.,non-inbred mouse cells) has not been altered prior to their use. That is, the non-inbred ES cells as obtained may contain alterations or mutations, but are not further modified to produce non-random or random mutations. The method comprises: (a) introducing mouse non-inbred pluripotent cells into mouse blastocysts, preferably tetraploid blastocysts, thereby producing mouse blastocysts containing mouse non-inbred pluripotent cells; (b) maintaining the product of (a) under conditions that result in production of embryos; (c) introducing an embryo or embryos (at least one/one or more embryos) into a foster mother, such as a pseudopregnant female mouse; and (d) maintaining the female into which the embryo(s) were introduced under conditions that result in development of live offspring, thereby producing a non-mutant mouse A variety of methods can be used to introduce mouse pluripotent cells, such as non-inbred mouse ES cells, into mouse tetraploid blastocysts. In one embodiment, this is carried out by injecting the non-inbred cells into tetraploid blastocysts, such as by microinjection, particularly piezo microinjection. Other methods can be used to introduce non-inbred ES cells into the blastocysts. For example, the method described by Amano et al., or a modification thereof, can be used. (Amano, T. et al., Theriogenology 53, 1449–1458 (2000)). Alternatively, any other method, such as a chemical method, which results in introduction of non-inbred ES cells into tetraploid blastocysts can be used.

Non-inbred pluripo:tent cells, such as non-inbred ES cells, used in the present method can contain at least one/one or more genetic alterations or mutations. Alternatively, as described above, non-inbred ES cells used can be non-mutant (have not been altered, after they are obtained, to contain a genetic alteration or mutation); such cells are used to produce non-mutant progeny by the method of the present invention. The genetic alterations or mutations that can be present in non-inbred ES cells used include, but are not limited to, transgenes (cDNA, genes or portions thereof), mutations (targeted or random), conditional mutations, targeted insertions of foreign genes, YAC and BAC sized transgenes, all or part of a chromosome, which may be from the same species as the embryo or another species, such as from a human. They include physical knockout of all or a part of a gene, functional knockout of a gene, introduction of a functional gene and introduction of DNA or a gene portion that changes the function/level of expression of a gene present in the ES cell (e.g., a promoter, enhancer or repressor). An important feature of the method of the present invention is that multiple genetic alterations, which will typically be consecutive genetic alterations but can also be simultaneous, can be made in the non-inbred ES cells, thus circumventing the need for breeding to combine multiple alterations in one animal, as is required if presently-available methods are used. Alterations can also be present in the non-inbred ES cells as they are obtained from the zygote from which they are derived. As used herein, the terms mutant non-inbred pluripotent cells, mutant non-inbred ES cells and similar terms encompass cells which comprise a mutation or mutations as obtained from the zygote which gave rise to the cells and cells which are mutated or altered after they are obtained from the zygote. Alterations can all be of the same type (e.g., all introduction of exogenous DNA) or of more than one type (e.g., introduction of exogenous DNA, gene knockout and conditional gene knockout). They can also be a combination of mutations present in the non-inbred ES cells as derived from a zygote and mutations made after they are derived from a zygote. The alterations made in genomic DNA of non-inbred ES cells can be chosen to produce a phenotype that is similar to (mimics) a condition that occurs in other species (e.g., humans) and the resulting mutant mice can, thus, serve as a model for that condition.

A variety of methods, known to those of skill in the art, can be used to alter or mutate inbred pluripotent (e.g., ES) cells to be used in the method of producing ES mice of the present invention. For example, an appropriate vector or plasmid can be used to introduce DNA into ES cells in order, for example, to integrate DNA into genomic DNA, express foreign DNA in recipient cells, cause recombination (homologous or nonhomologous) between introduced DNA and endogenous DNA or knock out endogenous gene(s), such as by means of the Cre-lox method. Alternatively, alterations or mutations can be produced by chemical methods or radiation. Gene targeting can also be used to produce mutant non-inbred pluripotent cells, such as mutant non-inbred ES cells. For example, the methodology described by Rideout and co-workers can be used. See, Rideout, W. M. et al. Nature Genetics 24, 109 (2000). And the references cited therein.

Tetraploid blastocysts can be produced by known methods, such as that described by James and co-workers. James, R. M. et al, Genet. Res. Camb. 60, 185, (1992) See also Wang, Z-Q et al, Mech. Dev. 62, 137 (1997) and the references cited therein.

Also the subject of this invention are mutant non-human mammals (e.g., mutant ES mice) produced by the method described herein; methods of producing non-human mammalian embryos; non-human embryos produced by the method; and a method of identifying a drug to be administered to treat a condition that occurs in a mammal, such as a human. The method of producing mutant non-human mammalian embryos comprises injecting non-human F1 ES cells into non-human tetraploid blastocysts and maintaining the resulting tetraploid blastocysts under conditions that result in formation of embryos, thereby producing a mutant non-human mammalian embryo(s). In one embodiment, the non-human mammalian embryo is a mutant mouse embryo.

Another embodiment of the present invention is a method of producing a non-human mammalian strain, such as a mouse strain, particularly a mutant mouse strain, that is derived from a given (single) ES cell clone, such as a mutant non-inbred ES cell clone, without outcrossing with a wild-type partner. Until now, it has not been possible to do so because each F1 ES cell line is of a given sex (generally male). However, fertile XO females have been produced from a male ES cell clone by in vitro selection for loss of the Y chromosome. As a result, a mutant mouse strain carrying all genetic alterations can be derived by breeding XY males and XO females, both derived from the same targeted ES cell clone and of identical genetic makeup without outbreeding of the mutant male to a normal female. Production of XY and XO subclones from the same clone, such as a clone carrying one or more genetic mutation or a multiply targeted clone, makes it possible to generate males and females carrying the same genetic alterations; such males and females can then be used to produce genetically identical offspring without the need for outbreeding.

For example, insertion of a negative selection marker (e.g., the Herpes Tk gene) on the Y chromosome of F1 ES cells makes it possible to derive XY and XO subclones from an initial male ES cell clone. The XO ES cells can be produced by inserting a Herpes Tk gene onto the Y chromosome by homologous recombination using known methods. For example, a vector that contains sequences homologous to a Y-linked gene (such as the Sry gene, the Mov15 gene or any other Y-linked gene) and expresses the Tk gene can be produced and introduced into ES cells. The cells are maintained under conditions that result in homologous recombination between vector sequences and Y chromosome sequences. The Tk gene is, as a result, introduced into the Y chromosome. The resulting cells can then be targeted or otherwise genetically altered. To generate an XO line from the clones, the cells are subjected to selection by culturing in the presence of gancyclovir, which results in killing of all cells carrying the Y chromosome into which the Tk gene has been inserted. The resulting males and females can be bred to produce offspring carrying the same genetic material (mutations) as the parents. Other negative selection markers, such as diphtheria toxin, can be used. In addition, because the Y chromosome is frequently lost spontaneously upon in vitro culture of ES cells, the mutant male F1 ES cells can be passaged and subclones screened for spontaneous loss of the Y chromosome. Fertile female mice have been produced from male F1 ES cells that have a male karyotype and are positive for Y-specific sequences by PCR in early passages. The B6×Balb line, V30.11 has produced 4/4 females who, as judged, for example, by their coat color, should be totally derived from male ES cells.

The method of the present invention is, thus, also a method of producing a mutant mouse by breeding a mutant male mouse and a mutant female mouse, wherein the male mouse and the female mouse (or an ancestor thereof) were produced from the same F1 male ES cells, such as from the same targeted male ES cell clone and the female mouse is an XO female. That is, the method is one of producing a mutant mouse strain by breeding a mutant male mouse and a mutant female mouse carrying identical genetic alterations as a result of having been derived from a single targeted male F1 ES cell clone. The mutant female mouse is XO and is produced (or is the progeny of an ancestor which was produced) by selecting for loss of the Y chromosome from a single (individual) male ES cell clone. The present invention also encompasses female mice which are XO and were produced from an F1 male ES cell, such as by knocking out of the Y chromosome. It also encompasses progeny produced by breeding a male and a female produced as described herein and progeny thereof.

The mutant non-human mammals, such as mutant mice, can be used as a model for a condition for which a preventive or therapeutic drug is sought. A method of identifying a drug to be administered to treat a condition in a mammal comprises producing, using the method of the present invention, a mutant mouse that is a model of the condition; administering to the mutant mouse a drug, referred to as a candidate drug, to be assessed for its effectiveness in treating or preventing the condition; and assessing the ability of the drug to treat or prevent the condition. If the candidate drug reduces the extent to which the condition is present or progresses or causes the condition to reverse (partially or totally), the candidate drug is a drug to be administered to treat the condition.

The present invention is illustrated by the following examples, which are not intended to be limiting in any way.

EXAMPLES

The following examples describe production of mice using inbred ES cells from four different ES cell lines from three inbred backgrounds (129/Sv, C57BL/6 and BALB/c) and six different F1 lines (129/Sv×C57BL/6, C57BL×129/Sv, BALB/c×129/Sv, 129/Sv×M. castaneus, C57BL/6× BALB/c and 129/Sv×FVB); assessment of pups produced using the two types of ES cells; and comparison of results obtained. The results show that use of F1 ES cells consistently results in production of viable mice, whether targeted or untargeted cells are used. They also demonstrate that genetic background is a crucial parameter for postnatal survival of pups derived from ES cells. Further, they demonstrate that the method of the present invention has been successfully used to produce mice that contain desired alterations without the need to produce and breed chimera en route to producing the desired non-chimeric pups.

Methods and Materials

The following methods and materials were used to produce mouse pups.

Production of ES cell clones.

Nuclear transfer of ES cell nuclei into enucleated metaphase II oocytes was carried out as previously described. (Wakayama, T. et al. Nature 394, 369–374 (1998); Wakayama, T. & Yanagimachi, R. Nature Genet. 22, 127–128 (1999);Ogura, A. et al. Biol. Reprod. 62, 1579–1584 (2000); Rideout, W. M. et al. Nature Genet. 24, 109–110 (2000);Wakayama, T. et al. Proc. Natl. Acad. of Sci. USA 96, 14984–14989 (1999). 1–3 hours after nuclear transfer oocytes were activated for 5 hours with 10 mM $Sr^{++}$in $Ca^{++}$free media in the presence of 5 mg/ml of Cytochalasin B. Embryos were cultured in vitro to the blastocyst stage and transferred to recipient mothers.

Embryo Culture

All embryo culture was carried out in microdrops on standard bacterial petri-dishes (Falcon) under mineral oil (Squibb). Modified CZB media (Chatot, C. L. et al., Biol. Reprod. 42, 432440 (1990)) was used for embryo culture unless otherwise noted. Hepes buffered CZB was used for room temperature operations while long term culture was carried out in bicarbonate buffered CZB at 37° C. with an atmosphere of 5% $CO_2$ in air Recipient Females and Cesarean Section.

Ten injected blastocysts were transferred to each uterine horn of 2.5 days post coitum pseudopregnant Swiss females that had mated with vesectomized males. Recipient mothers were sacrificed at E 19.5 and pups were quickly removed from the uterus. After cleaning fluid from their air passages, pups were placed under a warming light and respiration was observed. Surviving pups were fostered to lactating BALB/c albino mothers.

Culture of Embryonic Stem (ES) Cells

Derivation and culture of embryonic stem cells were carried out as previously described (Nagy, A. et al. Development 110, 815–821 (1990)) with ES cell lines derived from both inbred and F1 blastocysts. ES cells were cultured in DMEM with 15% FCS containing 1000 U/ml Leukocyte Inhibiting Factor (LIF) on gamma-irradiated primary feeder fibroblasts. For blastocyst injection ES cells were trypsinized, resuspended in DMEM and preplated on a standard 10 cm tissue culture dish for thirty minutes to remove feeder cells and debris.

Preparation of Two Cell Embryos for Electrofusion

B6D2F1 females were superovulated by IP injection of 7.5 IU PMS (Calbiochem) followed 46–50 hours later with 7.5 IU HCG (Calbiochem). After administration of HCG, females were mated with B6D2F1 males.). Fertilized zygotes were isolated 24 hours later. Zygotes were left in Hepes buffered CZB with 0.1% bovine testicular hyaluronidase for several minutes at room temperature to remove any remaining cumulus cells. After washing, zygotes were transferred to a new culture dish containing drops of bicarbonate buffered CZB and placed at 37° overnight to obtain two-cell embryos.

Preparation of Tetraploid Embryos by Electrofusion 40 hours post HCG the blastomeres of two-cell embryos were electrofused to produce one-cell tetraploid embryos. Electrofusion was carried out on in inverted microscope using the lid of a petri dish as a micro-manipulation chamber. Platinum wires were used as both electrodes and micro-manipulators to align two cell embryos for fusion. A group of 15 two-cell embryos was placed on the stage in a 200 ml drop of M2 media (Sigma). Embryos were aligned with the interface between their two blastomeres perpendicular to the electrical field and a single electrical pulse of 100V with a duration of 100 ms was applied to each individually. Manipulation of a single group took less then five minutes. After electrofusion, embryos were returned to CZB media at 37° C. Embryos that had not undergone membrane fusion within 1 hour were discarded.

Piezo Micromanipulator Injection of Tetraploid Blastocyts

For microinjection, 5–6 blastocysts were placed in a drop of DMEM with 15% FCS under mineral oil. A flat tip microinjection-pipette with an internal diameter of 12–15 um was used for ES cell injection. 15 ES cells were picked up in the end of the injection pipette. The blastocyst to be injected was held in the vicinity of the ICM with a standard holding pipette. The injection pipette, containing the ES cells was pressed against the zona opposite the inner cell mass. A brief pulse of the Piezo (Primatech Pmm, Ibaraki, Japan) was applied and the injection needle was simultaneously pushed through the zona and trophectoderm layer into the blastocoel cavity. The ES cells were then expelled from the injection pipette and pushed against the inner cell mass of the blastocyst. After injection of the entire group, blastocysts were returned to CZB media and placed at 37° until transfer to recipient females.

Example 1

Assessment of the Effects of Genetic Heterogeneity of Donor Cells on Development of ES Cell-Tetraploid Pups.

The possible effect of genetic heterogeneity of the donor cells on the development of ES cell-tetraploid pups was tested by transferring inbred or F1 ES cells into tetraploid blastocysts and assessing survival. Injection of ES cells into the blastocoel cavity of tetraploid blastocysts was aided by the use of a piezo-driven micromanipulator and the resulting composite embryos were transferred to recipient females. 312 tetraploid blastocysts were injected with four different inbred ES cell lines that gave rise to 20 pups (6%) that were alive and active at cesarean section. However, 17 of the 20 newborns died of respiratory failure within 30 minutes. Of the three remaining pups, two were unable to sustain respiration and died within the next few hours (Table 1). Only one inbred ES cell-tetraploid pup was able to sustain respiration and developed to adulthood In contrast, of 344 tetraploid blastocysts injected with 6 different F1 ES cell lines, 60 (18%) developed to birth, 51 of which (85%) survived to adulthood (Table 2). Thus, genetic heterogeneity of the donor ES cells has a significant effect on long-term survival of both nuclear clones and ES cell-tetraploid pups.

It has been previously shown that continued passage of ES cells is detrimental to their developmental potency (Wang, Z. Q, et al. Mech. Dev. 62, 137–145 (1997); Nagy, A. et al. Proc. Natl. Acad. Sci. USA 90, 8424–8428 (1993)). In order to assess whether continuous in vitro culture would impair the survival of F1 ES cell-tetraptoid pups, a 129Sv x C57BL/6 ES cell line (V6.5) was kept continuously in culture and injected into tetraploid blastocysts after prolonged passage. No impairment of postnatal survival of the resulting ES cell-tetraploid pups was noted after either 15 or 25 passages. In addition, F1 ES cell-tetraploid mice were produced from cells that had been subjected to two consecutive rounds of drug selection. First, selection with puromycin was used for isolating cells that carried a targeted insertion of a tet-transactivator gene in the Rosa26 locus. Second, hygromycin selection was used to isolate cells with a tet-inducible promoter driving expression of a hygromycin-thymidine kinase cassette in a random locus. Injection of these double-selected cells into 20 tetraploid blastocysts resulted in one full-term pup, which survived to adulthood (Table 2). The results described herein indicate that live, adult mice, entirely derived from ES cells can be generated from F1 ES cells even after long-term passage of the cells in culture or after consecutive rounds of drug selection.

Example 2

Histological Assessment of Lungs

ES cell-tetraploid pups derived from inbred ES cells appeared to suffer from respiratory distress after delivery. Histological analysis of both inbred and F1 completely ES cell derived neonates was carried out. Examination of the lungs from inbred ES cell-tetraploid pups revealed that the alveoli were not inflated, while the lungs of newborns derived from F1 ES cells were fully inflated. In addition, interstitial bleeding was often seen in inbred ES cell derived mice (data not shown). These observations suggest that the failure to initiate breathing and/or sustain normal circulation likely contributed to postnatal death of inbred ES cell-tetraploid pups Results described herein demonstrate that genetic heterozygosity is a crucial parameter influencing postnatal survival of pups derived from ES cells by tetraploid embryo complementation. Pups derived from inbred ES cells die perinatally with a phenotype of respiratory failure. In contrast, the great majority (80 to 85%) of pups derived from F1 ES cells survived to adulthood. The observed respiratory phenotype appears to be due to the inbred nature of the ES cell genome.

The possibility of deriving mice directly from ES cells without the production of a chimeric intermediate has great potential for facilitating the generation of animals with multiple genetic alterations. In conventional approaches, targeted ES cells are injected into diploid blastocysts to generate chimeric founders. The derivation of transgenic mice carrying the desired mutant allele requires out-crossing these chimeras with wild type mice. Thus, the generation of compound animals that combine multiple desired alleles or transgenes in their genome entails time-consuming and expensive cycles of crossing mice derived from different chimeric founders. In contrast, the ES cell-tetraploid technology in combination with F1 ES cells allows assembling multiple genetic alterations in the same ES cell line by consecutive gene targeting cycles in vitro prior to generating mutant animals. The desired transgenic mice with numerous genetic alterations can be derived in a single step by injecting the multiply targeted F1 ES cells into tetraploid blastocysts. Finally, unlike nuclear cloning technology, which has proven both difficult to master and transfer from laboratory to laboratory, the ES cell-tetraploid technology is easily adapted to any laboratory currently creating chimeric mice by ES cell blastocyst injection.

At present, the mechanisms that permit long-term survival of clones and ES cell-tetraploid pups derived from F1 but not from inbred ES cells are unclear. Though it is generally assumed that "hybrid vigor" is an important parameter in animal survival under various selective conditions, it is not apparent whether wide-ranging chromosomal heterozygosity or hetcrozygosity at only a few crucial modifier loci is required. Examining the potency of ES cells that have been derived from backcrosses between F1 mice and their parental inbred strains may clarify this question.

TABLE 1

Survival of Inbred ES Cell-Tetraploid Pups

| ES cell line | genotype | 4N blasts injected | Pups alive at term (% Inj) | Pups respirating after C-section (% Alive) | Pups suving to adult- hood (% Alive) |
|---|---|---|---|---|---|
| J1 | 129/Sv | 120 | 9(7.5) | 0 | 0 |
| V18.6 | 129/Sv | 48 | 5(10) | 1(26) | 0 |
| V26.2 | C57BL/6 | 72 | 3(4) | 1(33) | 0 |
| V39.7 | BALB/c | 72 | 3(4) | 1(33) | 1(33) |
| Total | Inbred | 312 | 20(6) | 3(15) | 1(5) |

TABLE 2

Survival of F1 ES Cell-Tetraploid Pups

| ES cell line | genotype | 4N blasts injected | Pups alive at term (% Inj) | Pups respirating after C-section (% Alive) | Pups suviving to adult- hood (% Alive) |
|---|---|---|---|---|---|
| V6.5 | C57BL/6 X 129/Sv | 72 | 18(25) | 17(94) | 16(89) |
| V6.5* | C57BL/6 X 129/Sv | 60 | 11(18) | 9(81) | 9(81) |
| V6.5** | C57BL/6 X 129/Sv | 20 | 1(15) | 1(100) | 1(100) |
| 129B6 | 129/Sv X C57BL/6 | 48 | 2(4) | 1(50) | 1(50) |
| F1.2-3 | 129/Sv X M. Cast. | 48 | 4(8) | 3(75) | 3(75) |
| V8.1 | 129/Sv X FVB | 24 | 7(30) | 7(100) | 7(100) |
| V17.2 | BALB/c X 129/Sv | 48 | 13(27) | 12(92) | 11(85) |
| V30.11 | C57BL/6 X BALB/c | 24 | 4(30) | 4(100) | 3(75) |
| Total | F1 | 344 | 60(18) | 54(90) | 51(85) |

*ES cell subclone targeted at the Rosa26 locus.
**ES cell subclone serially targeted once at the Rosa26 locus and once with a random insertion.

While the invention has been particularly shown and described with reference to particular embodiments thereof, it will be understood by those skilled in the art that various changes inform and details may be made therein without departing from the scope of the invention encompassed by the appended claims.

What is claimed is:

1. A method of producing a mouse, wherein mouse non-inbred ES cells are introduced into mouse tetraploid blastocysts by injection under conditions that result in production of an embryo and the resulting embryo is transferred into a pseudopregnant female mouse which is maintained under conditions that result in development of live offspring.

2. The method of claim 1, wherein injection is piezo microinjection.

3. A method of producing a mouse embryo comprising injecting mouse non-inbred ES cells into mouse tetraploid blastocysts and maintaining the resulting tetraploid blastocysts under conditions that result in formation of embryos, thereby producing a mouse embryo.

4. The method of claim 3, wherein the mouse non-inbred ES cells are mutant mouse non-inbred ES cells and are injected into mouse tetraploid blastocysts by piezo microinjection.

5. A method of producing a mutant mouse, wherein mouse non-inbred pluripotent ES cells comprising at least one mutation in genomic DNA are introduced into mouse tetraploid blastocysts by injection under conditions that result in production of an embryo and the resulting embryo is transferred into a foster mother which is maintained under conditions that result in development of live offspring, thereby producing a mutant mouse, wherein said foster mother is a mouse.

6. The method of claim 5, wherein injection is piezo microinjection.

7. A method of producing a mutant mouse embryo comprising injecting mutant mouse non-inbred ES cells into mouse tetraploid blastocysts and maintaining the resulting tetraploid blastocysts under conditions that result in formation of embryos, thereby producing a mutant mouse embryo.

8. The method of claim 7, wherein mutant mouse non-inbred ES cells are injected into mouse tetraploid blastocysts by piezo microinjection.

9. A method of producing a mutant mouse, comprising: (a) introducing mouse non-inbred ES cells comprising at least one mutation in genomic DNA into mouse tetraploid blastocysts by injection, thereby producing mouse blastocysts containing mouse non-inbred ES cells; (b) maintaining the product of (a) under conditions that result in production of embryos; (c) introducing an embryo into a pseudopregnant female mouse; and (d) maintaining the female mouse into which the embryo is introduced under conditions that result in development of live offspring, thereby producing a mutant mouse.

10. The method of claim 9, wherein injection is piezo microinjection.

11. The method of claim 10, wherein the at least one mutation in genomic DNA is a gene knockout or exogenous DNA incorporated into the genomic DNA.

12. A method of producing a mutant mouse that is derived from a single non-inbred ES cell clone, comprising breeding a mutant male mouse and a mutant female mouse, wherein the male mouse and tile female mouse or an ancestor thereof were produced from the same non-inbred male ES cell clone and the female mouse is an XO female.

13. The method of claim 12, wherein the non-inbred ES cell clone is a non-inbred F1 cell clone.

14. A method of producing mouse XO F1 ES cells, comprising introducing into mouse male F1 ES cells a negative selection marker, under conditions appropriate for insertion of the negative selection marker in the Y chromosome of mouse F1 ES cells, thereby producing a mixture of mouse F1 ES cells comprising F1 ES cells in which the negative selection marker is inserted in the Y chromosome and other F1 ES cells, some of which do not contain a Y chromosome; subjecting the resulting mixture to conditions that result in the death of F1 ES cells in which the Y chromosome has the negative not result in the death of F1 ES cells that lack a Y chromosome and are XO F1 ES cells, thereby producing mouse XO F1 ES cells.

15. A method of producing a mutant mouse strain, comprising breeding a mutant male mouse and a mutant female mouse, wherein the mutant male mouse and the mutant female mouse or an ancestor thereof were derived from the same non-inbred male mouse ES cell clone and the mutant female mouse is an XO female.

16. The method of claim 15, wherein the non-inbred male mouse ES cell clone is an F1 male mouse ES cell.

17. The method of claim 16, wherein the mutant XO female mouse or an ancestor thereof was derived from a male mouse F1 ES cell by knocking out the Y chromosome of the F1 ES cell, thereby producing an XO F1 ES cell; introducing the XO F1 ES cell into a tetraploid mouse blastocyst under conditions that result in production of an embryo and transferring the resulting embryo into a foster mother which is maintained under conditions that result in development of live offspring, thereby producing an XO female offspring.

* * * * *

UNITED STATES PATENT AND TRADEMARK OFFICE
CERTIFICATE OF CORRECTION

PATENT NO. : 6,784,336 B2 Page 1 of 1
DATED : August 31, 2004
INVENTOR(S) : Kevin C. Eggan and Rudolf Jaenisch It is certified that error appears in the above-identified patent and that said Letters Patent is hereby corrected as shown below:

Title page,
Item [54], Title, delete "MUTANT MICE", and insert -- NON-HUMAN MAMMALS --.

Column 12,
Line 60, delete "tile", and insert -- the --.

Column 13,
Line 8, after "negative", and insert -- selection marker inserted therein and do --.

Signed and Sealed this

Fifteenth Day of March, 2005

JON W. DUDAS
*Director of the United States Patent and Trademark Office*